(12) United States Patent
Trifonov et al.

(10) Patent No.: US 10,517,904 B2
(45) Date of Patent: Dec. 31, 2019

(54) METHOD FOR PREPARING AN ADSORBED DRONE BROOD AND THE COMPOSITION THEREOF

(75) Inventors: Vyacheslav Nikolaevich Trifonov, Zarechni (RU); Julia Anatoljevna Elistratova, Penza (RU); Konstantin Gennadievich Elistratov, Penza (RU); Natalia Vyacheslavovna Kurus, Penza (RU); Irina Vladimirovna Homykova, Penza (RU); Tatiana Viktorovna Elistratova, Penza (RU); Lilia Alexandrovna Burmistrova, Hodynino (RU)

(73) Assignee: Parapharm LLC, Penza (RU)

( * ) Notice: Subject to any disclaimer, the term of this patent is extended or adjusted under 35 U.S.C. 154(b) by 0 days.

(21) Appl. No.: 14/345,243

(22) PCT Filed: Jul. 5, 2012

(86) PCT No.: PCT/RU2012/000542
§ 371 (c)(1),
(2), (4) Date: Mar. 15, 2014

(87) PCT Pub. No.: WO2013/039424
PCT Pub. Date: Mar. 21, 2013

(65) Prior Publication Data
US 2015/0030640 A1    Jan. 29, 2015

(30) Foreign Application Priority Data
Sep. 16, 2011 (RU) .................. 2011137992

(51) Int. Cl.
*A61K 35/64* (2015.01)
*A61K 47/26* (2006.01)

(52) U.S. Cl.
CPC .............. *A61K 35/64* (2013.01); *A61K 47/26* (2013.01)

(58) Field of Classification Search
None
See application file for complete search history.

(56) References Cited

FOREIGN PATENT DOCUMENTS

CN    1369271 A   *   9/2002
RU    2412616 C1   *   2/2011

OTHER PUBLICATIONS

Lebedev (Pchelovodstov (2003), No. 3, pp. 52-54—English translation).*

* cited by examiner

*Primary Examiner* — Susan Hoffman
(74) *Attorney, Agent, or Firm* — Patentagar PLLC; Alexander Rabinovich

(57) ABSTRACT

The invention relates to the pharmaceutical and food industries, to medicine, and in particular, to biologically active food supplements, and describes the process of obtaining an adsorbed drone brood, and the composition thereof that ensures the preservation and stabilization of all biological properties of the drone brood over a long period (up to three years), which makes it possible to organize the mass production of drone brood-based products.

1 Claim, No Drawings

METHOD FOR PREPARING AN ADSORBED DRONE BROOD AND THE COMPOSITION THEREOF

CROSS-REFERENCE TO RELATED APPLICATIONS

This application is a U.S. national stage application of an international application PCT/RU2012/000542 filed on 5 Jul. 2012, published as WO/2013/039424, which international application claims priority of a Russian Federation patent application RU2011137992 filed on 16 Sep. 2011.

FIELD OF THE INVENTION

The invention relates to the pharmaceutical and food industries, to medicine, and in particular, to biologically active food supplements, and describes the process of obtaining an adsorbed drone brood, and the composition thereof that ensures the preservation and stabilization of all biological properties of the drone brood over a long period (up to three years), which makes it possible to organize the mass production of drone brood-based products.

BACKGROUND OF THE INVENTION

In Romania it is patented the method of obtainment of biologically active product from drone larvae or working bees or queens (Patent RO No 74872/1980), which is biologically active substance for obtainment of medicines and cosmetic means. It is known the patent RU No 22402930 "Method of preparation of the fodder supplement from drone larvae for increase of dogs' organisms resistance by parasitosis". It is known the patent RU No 2258522 "The method of preparation making from drone larvae for stimulation of animal organism". It is known the patent RU No 2395289 "The method of making of biogenic stimulator from the larvae of drone brood of bees". It is known the patent No 2245155 COMPOSITION OF THE CANNED HOMOGENATE OF THE BEES BROOD (DRONE BROOD AND QUEEN LARVAE). The given substance is considered by us as a prototype.

Homogenate of larvae represents by itself an available, cheap, perspective source of obtainment of medical-preventative means and food means. Neutral medium of the brood and also presence of nutritious substances, certainly, favors development of microorganisms and fungi that leads to rapid spoilage of the raw material by its improper storage. Inclusion in the prototype of sorbine and lemon acid stabilizes drone brood, nevertheless, acids influence negatively on biological active components of the drone brood, leading to its destruction that impoverishes biological value of the prototype. The drawback of prototype is also that the prototype should be stored in a refrigerator that leads considerable material expenses. Also the term of prototype storage is one year only that limits its using in the pharmaceutical industry.

The given invention is distributed on the production of the drone brood adsorbed that is prepared from homogenate of the drone brood and adsorbent via mixing up to uniform mixture. Lactose, glucose, fructose or products on their base and also mixture or mixtures of the given products can serve as absorbents.

Homogenate of the drone brood is obtained most often by pressing (squeezing) of pieces of honeycomb with drone larvae, just sealed or yet open on 7-th-11-th day. After the pressing it is obtained dense liquid with peculiar taste—larval milk. Larvae of drones the best of all to get by the aid of the special drone honeycombs. They sufficiently diminish wasteful expenses of work, simplify mechanization of the larvae selection and give possibility to use their cells iteratively. Honeycombs with drone larvae, sealed by wax lids, are retrieved from nests and are carried in the special premise. All the manipulations by the larvae collection, preparation, canning, prepacking of homogenate in vials from the dark glass and package are carried without fail in sanitary-hygienic conditions, responding to demands, lodging to the production of medical preparations and food products. The vessels and the equipment are washed by clean water and sterilized by spirit or are boiled during one hour. The work is carried in the white coat, special hat and gauze bandage from 4 layers, closing mouth and nose. One day before sealing of honeycomb cells, in which drone larvae are developed, they are retrieved and homogenized. It is obtained yellowish mass with a nice specific smell and sourish taste.

Wax lids of the sealed brood are carefully cut by electric, steam or apiarist knife, warming in the boiled water. Afterwards the honeycombs are placed in honey centrifuge. During 10-12 minutes up to 95% of larvae are retrieved. When building frames are used, it is possible simultaneously to retrieve larvae via pressing and to prepare homogenate.

The homogenate obtained is adsorbed immediately.

The process of adsorbing is the following:

The adsorbing of the drone brood is realized via thorough grinding manually or mechanically in non-metallic (porcelain) mortar of the one part of fresh prepared homogenate with 3-30 parts of adsorbent (by the weight).

Grinding should be provided in the short interval of time and no latter than 55 minutes from the moment of retrieval from the honeycombs. The term no more than 55 minutes does not permit to spoil the brood. After 55 minutes decay of the drone brood begins. In order to keep the brood from surplus influence of the rays of light, oxygen, air and temperature of surrounding medium, it is worth to hold the lesser range. The semiproduct obtained is crushed. Afterwards it is placed for drying in a vacuum-chamber. The drying is realized in the vacuum without application of temperature (without warming). The duration of drying is dependent on mass loaded: the greater is the mass, the longer is the drying. During the period of drying it is necessary to constantly check readout of vacuum-meter that should not be lower than 1 mm of mercury column.

The product obtained is retrieved from the vacuum-chamber with humidity up to 1.5%, and it is placed in tightly closed vessels, impervious to the light (for example, glass jar of orange color or other kinds of package according to the current Normative and Technical Documentation, providing safety and quality of the product and permitted to application by organs of State Sanitary Epidemic Control of the Russian Federation).

The product obtained may be stored about three years. In the pharmaceutical industry lactose serves as the adsorbent since it does not sinter by pelletization. For the food industry, in private for drinks preparation, glucose or fructose serve, since the lactose does not dissolved in the water.

It is admitted also any mixture of the given products for other industries.

The range of 3-30 parts of adsorbent is explained in the following way:

Less than 3 parts—does not provided preserving effect of the adsorbent.

More than 30 parts—it is lost biological value of the product prepared and there are appeared complications with its further use as the substance, e.g., in the pharmaceutical industry—for provision of the pharmacologic activity it will be necessary to put greater mass of the product that will lead to the greater size of a tablet and complication with its usage by man.

The invention claimed is:

1. A method of preparing absorbed drone brood, the method comprising the steps of:
providing drone brood;
homogenizing the drone brood to obtain drone brood homogenate;
providing adsorbent;
mixing the drone brood homogenate with the adsorbent;
adsorbing the homogenate in the mixture;
subjecting the adsorbed homogenate to vacuum drying;
said homogenizing being performed by extracting drone larvae from honeycombs by pressing drone larvae honeycombs;
said adsorbent comprising lactose, or glucose, or fructose, or a combination thereof;
said mixing being performed with one weight part of the homogenate and 3-30 weight parts of the adsorbent;
said adsorbing taking place no later than 55 minutes after said extracting and being performed by thorough grinding the homogenate and the adsorbent;
said vacuum drying being performed under pressure no less than 1 mm Hg, lasting until the adsorbed drone brood achieves humidity up to 1.5% and being performed with no warming applied.

* * * * *